(12) United States Patent
Carlos Fuentevilla

(10) Patent No.: US 12,257,354 B2
(45) Date of Patent: Mar. 25, 2025

(54) DEVICE FOR SANITIZING GARMENTS AND PERSONAL ITEMS

(71) Applicant: Gustavo Adolfo Carlos Fuentevilla, Nuevo Leon (MX)

(72) Inventor: Gustavo Adolfo Carlos Fuentevilla, Nuevo Leon (MX)

( * ) Notice: Subject to any disclaimer, the term of this patent is extended or adjusted under 35 U.S.C. 154(b) by 835 days.

(21) Appl. No.: 17/393,467

(22) Filed: Aug. 4, 2021

(65) Prior Publication Data
US 2022/0339306 A1  Oct. 27, 2022

(51) Int. Cl.
*A61L 2/10* (2006.01)
*A61L 2/26* (2006.01)

(52) U.S. Cl.
CPC ..................... *A61L 2/10* (2013.01); *A61L 2/26* (2013.01); *A61L 2202/11* (2013.01); *A61L 2202/122* (2013.01); *A61L 2202/14* (2013.01); *A61L 2202/26* (2013.01)

(58) Field of Classification Search
CPC .......... A61L 2/10; A61L 2/26; A61L 2202/11; A61L 2202/122; A61L 2202/14; A61L 2202/26
See application file for complete search history.

(56) References Cited

U.S. PATENT DOCUMENTS

| | | | |
|---|---|---|---|
| 6,646,270 B2 | 11/2003 | Cunningham | |
| 10,874,756 B1* | 12/2020 | Guerrero | A61L 2/28 |
| 2002/0115585 A1* | 8/2002 | Hei | A61L 2/0035 |
| | | | 422/68.1 |
| 2003/0017073 A1* | 1/2003 | Eckhardt | A61L 2/10 |
| | | | 422/24 |
| 2004/0099812 A1* | 5/2004 | Humphreys | A61L 2/04 |
| | | | 250/455.11 |
| 2010/0266445 A1* | 10/2010 | Campagna | A61L 2/202 |
| | | | 422/23 |
| 2013/0019697 A1* | 1/2013 | McKeen | G01N 35/00029 |
| | | | 73/863.21 |
| 2016/0101202 A1* | 4/2016 | Gil | A61L 2/10 |
| | | | 250/455.11 |
| 2019/0099509 A1* | 4/2019 | Martz | A61L 2/10 |
| 2019/0374075 A1* | 12/2019 | Barnett | A61L 2/10 |
| 2020/0008583 A1* | 1/2020 | Gunura | A47C 9/10 |
| 2020/0309703 A1* | 10/2020 | Luk | G08B 3/10 |
| 2020/0397935 A1* | 12/2020 | Church | G06F 3/0482 |
| 2021/0308296 A1* | 10/2021 | Cook | A47B 49/008 |

(Continued)

FOREIGN PATENT DOCUMENTS

| | | |
|---|---|---|
| CN | 87214861 | 7/1988 |
| CN | 2155876 | 2/1994 |
| WO | WO2015080768 | 6/2015 |

*Primary Examiner* — Regina M Yoo
(74) *Attorney, Agent, or Firm* — Defillo & Associates, Inc; Evelyn A. Defillo

(57) ABSTRACT

The present invention corresponds to a device in which garments such as clothing, personal objects such as wallets, watches, shoes, coins are placed among a large number of objects, which have been carried as personal objects by a user and that by some reason they were exposed to microorganisms such as viruses, bacteria and other pollutants found in the environment; Because these microorganisms use air or saliva, sweat, among other fluids that act as vectors and therefore personal objects have a high risk of being contaminated without the user noticing it visually or with any ease.

4 Claims, 4 Drawing Sheets

(56) References Cited

U.S. PATENT DOCUMENTS

| | | | |
|---|---|---|---|
| 2021/0361810 A1* | 11/2021 | Glanz | A61L 2/0005 |
| 2021/0402026 A1* | 12/2021 | Dobrovolsky | A61L 2/10 |
| 2022/0032345 A1* | 2/2022 | Maloley | A61L 2/10 |
| 2022/0054674 A1* | 2/2022 | Gadotti Martins | A61L 2/202 |
| 2022/0202980 A1* | 6/2022 | Frantz | A61L 2/10 |
| 2022/0249717 A1* | 8/2022 | Forhan | A61L 2/202 |

* cited by examiner

DEVICE FOR SANITIZING GARMENTS AND PERSONAL ITEMS

FIELD OF THE INVENTION

The present invention corresponds to a device in which garments such as clothing or personal items as wallets, watches, shoes, coins among a large number of objects that have been carried as personal items by a user and for any reason were exposed to microorganisms such as viruses, bacteria and other pollutants that are found in the environment; Because these microorganisms use air or saliva, sweat, among other fluids that act as vectors and therefore personal objects have a high risk of being contaminated without the user noticing it visually or with any ease. The device works mechanically and is therefore considered to be an invention in this field.

BACKGROUND

In the state of technique, we can find some devices that are used to sanitize garments such as the following patents:

CN87214861U whose name is a portable UV bacteria sterilizing lamp, which consists of a model that discloses a portable ultraviolet sterilizing lamp, comprising a DC transistor transformer a U type ultraviolet sterilizing lamp, a sterilizer box, dry cells, etc., and overcoming the defects that limited the power source and accessories of the common ultraviolet sterilizing lamp, the common ultraviolet sterilization lamp can only be fixed indoors so as to be inconvenient for movement and can only be used for hospital departments, pharmacy departments, etc. Disengaged from the commercial power supply; the utility model can widely applied to personally or collectively sterilize tableware and food with bacteria at any time before dining at home or in public places, and is even more suitable for sterilizing medical instruments outdoors, in the field, with the family, etc. The utility model has a sterilization rate that reaches 100% in six minutes, the cost which is only 30% of the common ultraviolet sterilizing lamp, and the most convenient manufacture and use; however, since this technology is not installed in a controlled environment, it does not guarantee proper sanitization because of whether the environment in which it is applied is contaminated, then it becomes contaminated again and immediately.

Another document is the CN2155876Y that discloses a functional ultraviolet ray sterilizer that is used for the sterilization of carpets, bedding, clothes, diapers, fruits, vegetables, cutlery, floor and walls. This utility model is characterized in that an ultraviolet ray sterilizer is arranged in a box with an upper lid. An ultraviolet lamp tube is controlled to be on or off through a double fuze switch. The bottom of the top cover box is a circular section. When the circular section is connected to a carpet, the light is not leaked, so the human body is safe. A lower base box that can be placed with sterilization items is matched with the bottom part of the upper cover box to form a closed system to carry out sterilization. So, the utility model not only has a good effect of sterilization, but also is added with a plurality of functions. However, it shows the same defect as the previous one.

Controlling the environment is essential to prevent personal items from being contaminated again and some of the developments that show this type of control are the following:

U.S. Pat. No. 6,646,270B2, which discloses disclose a germicidal mailbox that receives the mail in an internal rotatable cage and tumbles such mail while irradiating it with ultraviolet light at a wavelength of 254 nanometers to kill or render inert microbes on the mail that could carry diseases to which humans are susceptible. After the mail has been tumbled and irradiated, it is safe for handling by humans without the danger of infection and disease from microbes that may purposefully, through terrorism, or accidentally; have become attached to the mail; this type of invention works, only in this case it is limited to the mailbox in such a way that only the correspondence is sanitized, as long as it is placed inside the mailbox but when it comes to packages of considerable size or that exceed the dimensions of the mailbox, it is common for postmen or courier and mail deliverymen to leave it out in the open without being able to sanitize it.

Publication WO2015080768 claims ultraviolet (UV) devices, systems, and methods for ultraviolet (UV) disinfection and sterilization of a container, room, space, or defined environment. The systems, UV devices, and methods are particularly useful for the UV disinfection and sterilization of a container used in the food and dairy industry and for containers used in the process of fermentation for an alcoholic beverage. Provided also UV devices, systems, and methods for inhibiting "the growth of one or more species of microorganisms present in a container, room, space or defined environment, preferably for inhibition the growth of the one or more species of microorganisms present on an interior surface of a container, room, space or defined environment; being this invention, the one that is considered the closest to the invention that is proposed, however, its components are different since this invention includes: a) a light source, a frame that is attached to the germicidal (UV) light source, a specific method of placing the germicidal (UV) light source in a desired position within a container and a circuit board that controls one or more functionalities of the portable UV device.

To analyze the specific sanitizing methods, the present invention refers to a device that specifically involves UV rays.

It is conventional to the knowledge that has developed in the world that ultraviolet (UV) light has germicidal properties.

Ultraviolet light kills microorganisms, directly affecting the genetic material of microorganisms that are exposed to this type of rays. Wavelengths between 200 and 300 nm have been shown to initiate a photoreaction between adjacent pyrimidines. Pyrimidine bases, such as cytosine and thymine, have conjugated double bonds and as such absorb ultraviolet light. Photoreaction between adjacent thymine or cytosine bases occurs at an excessively fast rate (on the order of picoseconds). There are two possible products. The most common is the formation of a cyclobutane ring between the two pyrimidines. The other photoproduct is a (6-4) pyrimidone. The formation of these dimers leads to "kinks" within the formation of proper transcriptional and replication templates. Cyclobutane cytosine photodimers are susceptible to deamination and therefore can induce point mutations, especially the CC (two adjacent cytosines) become TT (two adjacent thymines) through the SOS response system in both eukaryotic and prokaryotes. Inactivation of specific genes through point mutations is one of the mechanisms by which UV rays-induced genetic damage can lead to cell death, inhibiting cell replication.

However, the microorganism in this DNA has a maximum UV light absorption at 253.7 nm. It has been determined that approximately 26,400 microwatt-seconds/cm 2 is needed to disable 100% of the most resistant bacteria.

UV light is divided into 3 different categories: UV-A (315-400 nm), UV-B (280-315 nm) and UV-C (200-280 nm) Considering DNA optimally absorbs UV light at 253.7 nm, it is UV-C lamps that are used in most of the germicidal devices of the previous technique. UV devices are used, for example, to inactivate microorganisms in laboratory environments.

There is a need in the technique for non-toxic and non-cancerogenic methods, systems, and compositions useful for the sterilization of containers and, in particular, for the sterilization of personal items. There is also a need to provide enhance UV devices, systems, and methods in the face of pandemics such as COVID 19 and exposure to other microorganisms with related vectors such as *Agrobacterium tumefaciens*, Adenovirus Type III, *Aspergillus Amstelodami*, *Aspergillus flavus*, *Aspergillus glaucus*, *Aspergillus niger*, *Bacillus Anthracis*, *Bacillus Anthracis* (spores), *Bacillus megatherium* SP, *Bacillus megatherium* SP (spores), *Bacillus paratyphosus*, *Bacillus subtilis*, *Bacillus subtilis* (spores), Bacteriophage, *Campylobacter jejuni*, *Chlorella vulgaris* (Algae), Cyanobacteria sp., *Clostridium botulinum*, *Clostridium tetani*, *Corynebacterium diphtheriae*, Coxsackie, *Cryptosporidium parvum*, *Dysentery bacilli*, *E. histolytica*, *Eberthella typhosa*, Echovirus I (Picomaviridae), Echovirus II (Picornaviridae), *Enterococcus faecalis*, *Escherichia Coli* (*E. Coli*), *Giardia lamblia*, Nematode eggs (helmintos), Influenza (orthomyxoviridae), *Legionella bozemanii*, *Legionella dumofii*, *Legionella gormanii*, *Legionella longbeachae*, *Legionella micdadei*, *Legionella pneumophila*, *Leptospira canicola*, *Leptospira interrogans*, *Listeria monocytogenes*, *Micrococcus candidus*, *Micrococcus sphaeroides*, Tobacco mosaic (TMV), *Mucor Mucedo*, *Mucor Racemosus* (A&B), *Mycobacterium tuberculosis*, *Neisseria—Moraxella catarrhalis*, *Oospora lactis*, *Paramecium* sp., *Penicillium chrysogenum*, *Penicillium digitatum*, *Penicillium expansum*, *Penicillium roqueforti*, *Phytomonas tumefaciens*, Poliovirus (picomaviridae), *Proteus vulgaris*, *Pseudomonas aeruginosa*, *Pseudomonas fluorescens*, *Rhizopus nigricans*, *Rhodospirillum rubrum*, Rotavirus (Reoviridae), *Saccharomyces cerevisiae*, *Saccharomyces ellipsoideus*, *Saccharomyces* sp., *Salmonella enteritidis*, *Salmonella paratyphi*, *Salmonella* Species, *Salmonella typhi*, *Salmonella typhimurium*, *Sarcina lutea*, *Serratia marcescens*, *Shigella dysenteriae*, *Shigella flexneri*, *Shigella dysenteriae*, *Shigella sonnei*, *Spirillum rubrum*, *Staphylococcus albus*, *Staphylococcus aureus*, *Staphylococcus epidermidis*, *Streptococcus haemolyticus*, *Streptococcus lactis*, *Streptococcus pyogenes*, *Streptococcus salivarius*, *Streptococcus viridans*, *Trichosporon*, Variola Virus (Poxviridae), *Vibrio cholerae*, *Vibrio comma*, Hepatitis A Virus (HAV), Hepatitis B Virus (HBV), *Yersinia Enterocolitica* among others, which contaminate by exposure of liquids emitted by the saliva of contaminated people or by placing them on a contaminated surface.

The present invention does not focus on sanitizing the surfaces where personal objects are placed, but rather on placing personal objects in front of the device, preferably before introducing them to a controlled environment, such as hospitalization rooms, house-rooms, offices, etc., and thereby guarantee that the virus to which the personal objects were exposed will not be introduced into these spaces.

SUMMARY

The characteristic detail of this novel device for sanitizing garments and personal items are clearly shown in the following description and the figures, where the same reference signs are followed to indicate the parts and figures shown.

DESCRIPTION

Figure 1:
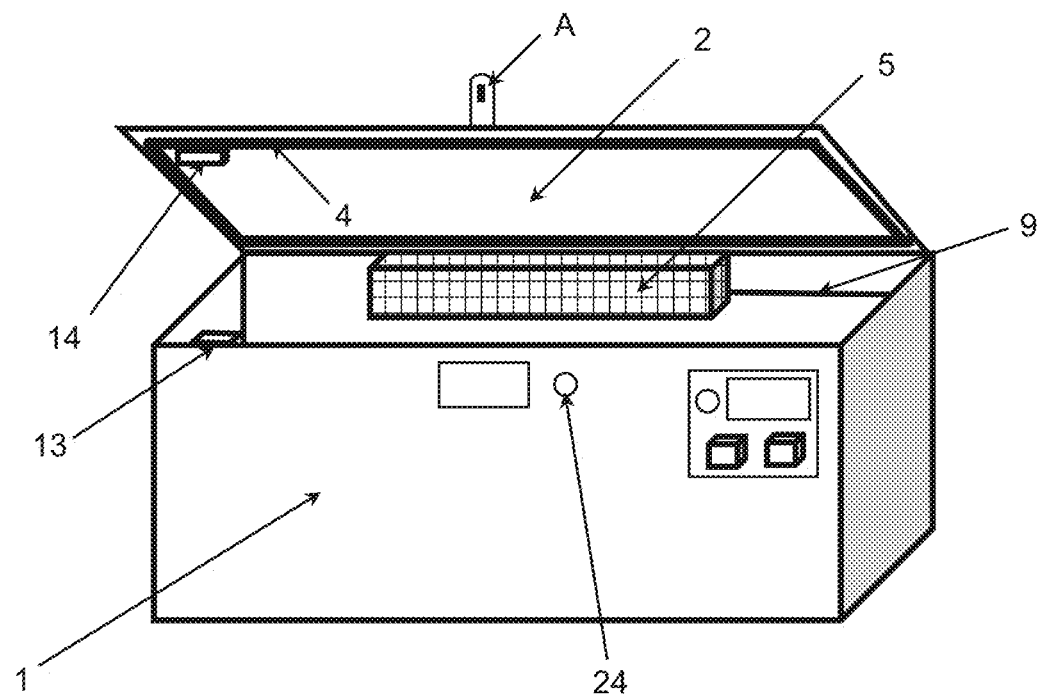
FIG. 1 is a conventional front perspective view with the lid folded down to show the international components of the device for sanitizing garments and personal items.
Figure 2:
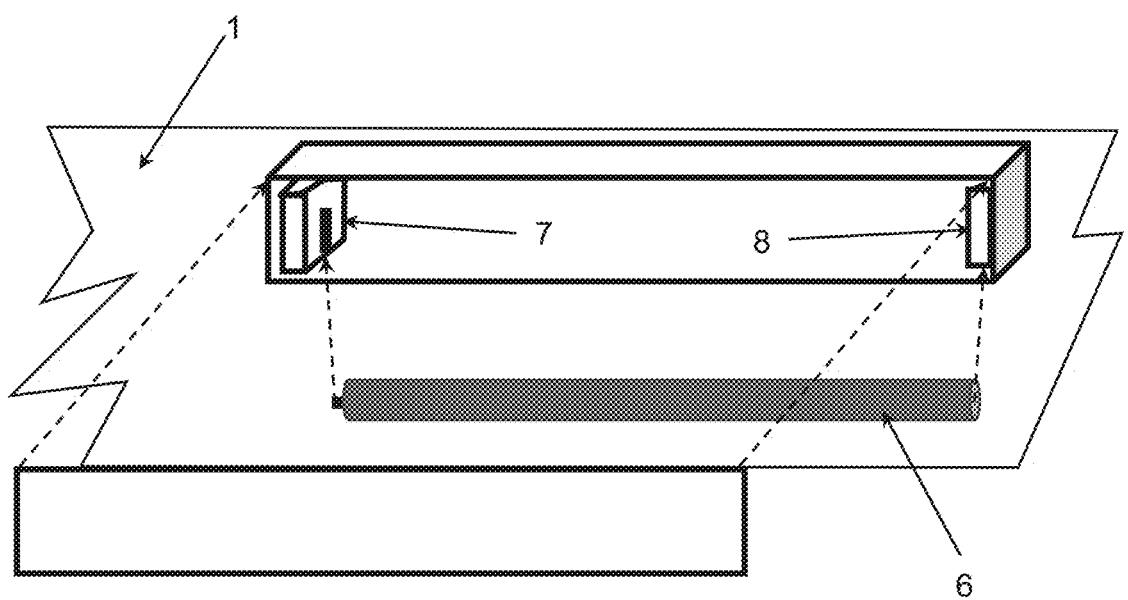
FIG. 2 is a conventional perspective close-up and sectioned view of the device for sanitizing garments and personal items, highlighting the components of the cover of the UV rays emitting source.
Figure 3:
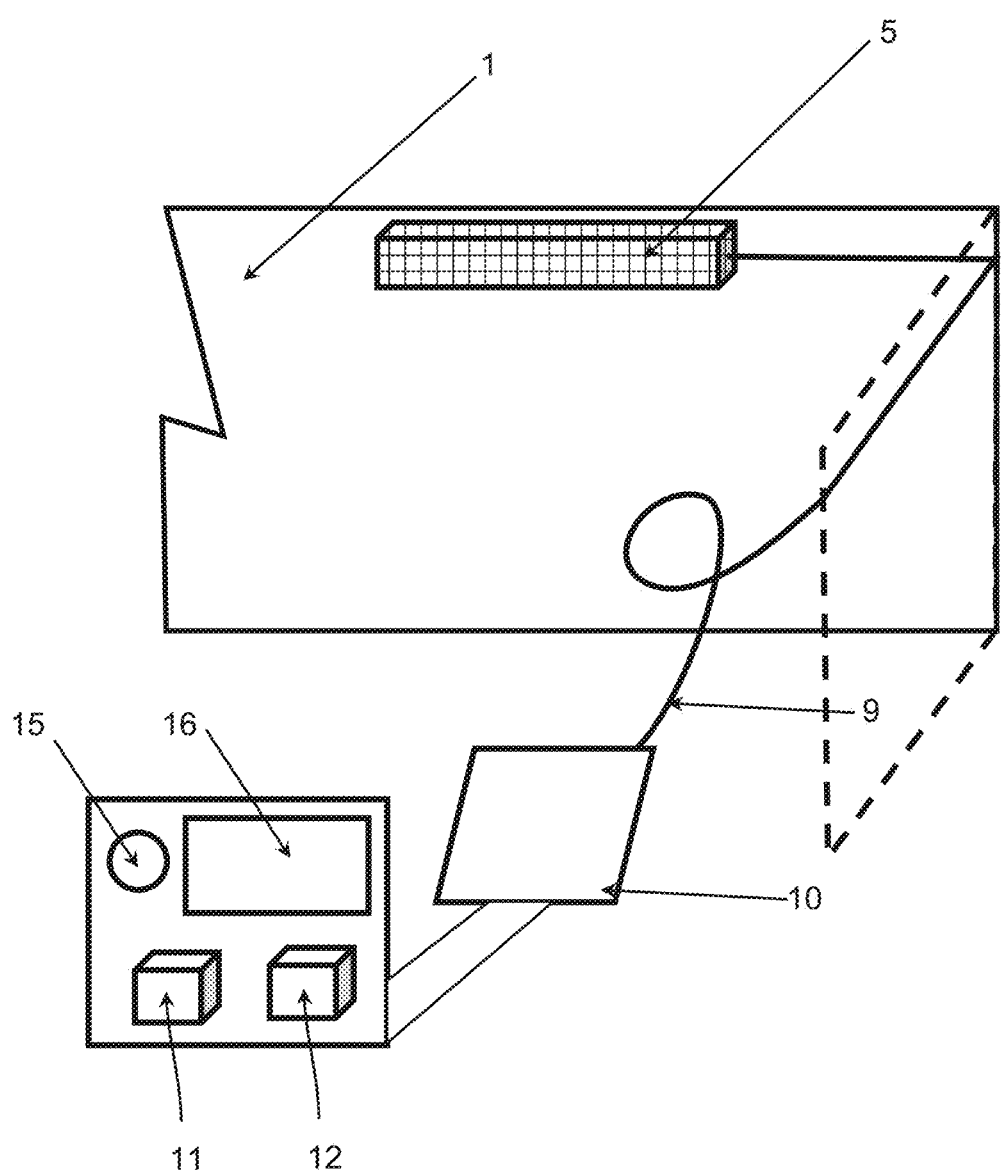
FIG. 3 is a conventional perspective close-up and sectioned view of the device for sanitizing garments and personal items, highlighting the components of the cable, the electronic card and its external controls.
Figure 4:
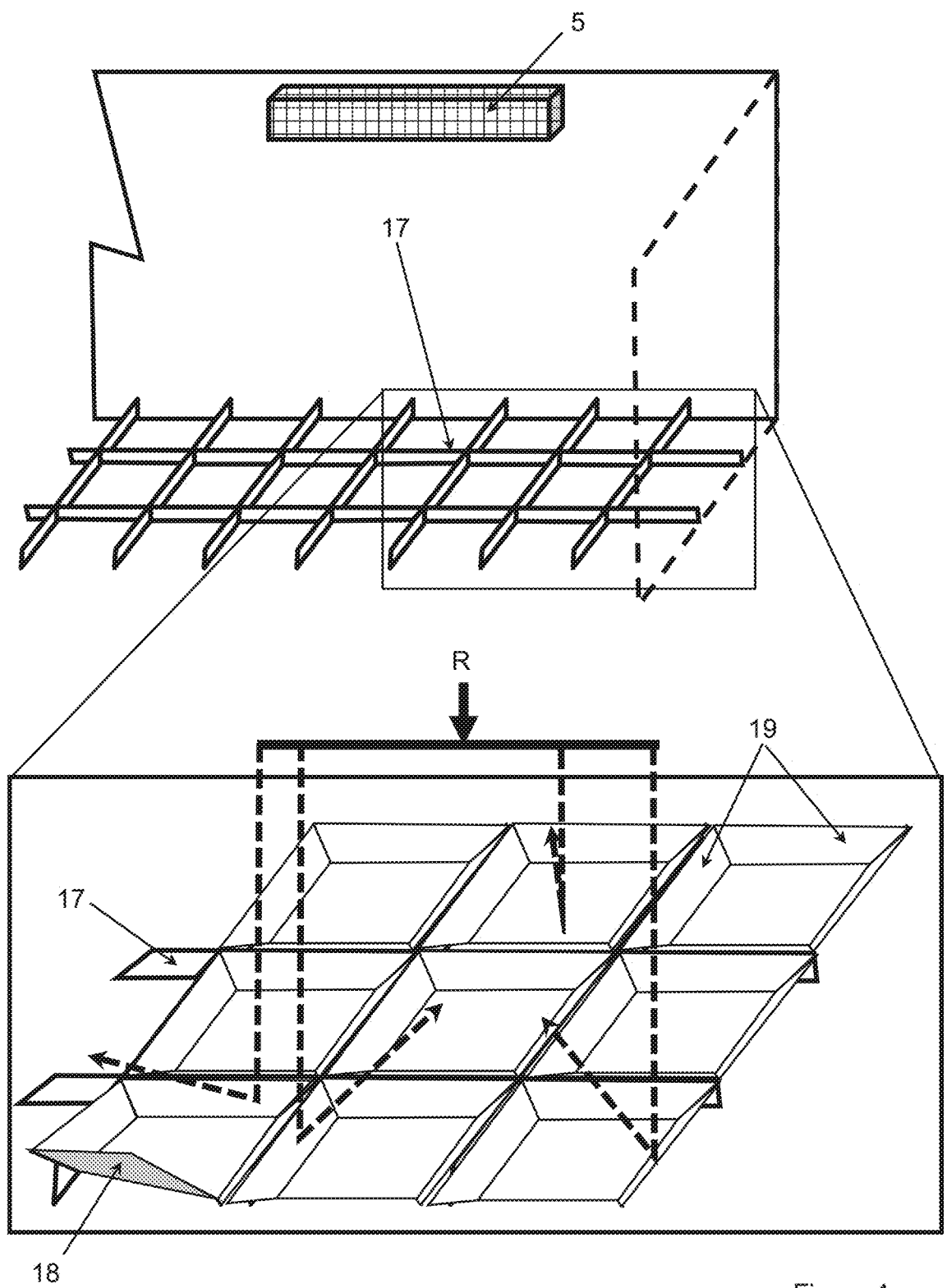
FIG. 4 is a conventional perspective view with a "rectangular fisheye" approach of the interior of the sectioned box, where the way in which the rays are distributed from the source is simulated when they are reflected in the inclinations of all the sides of the interior prismatic figures either the cover, the base grid and all sides.
Figure 5:
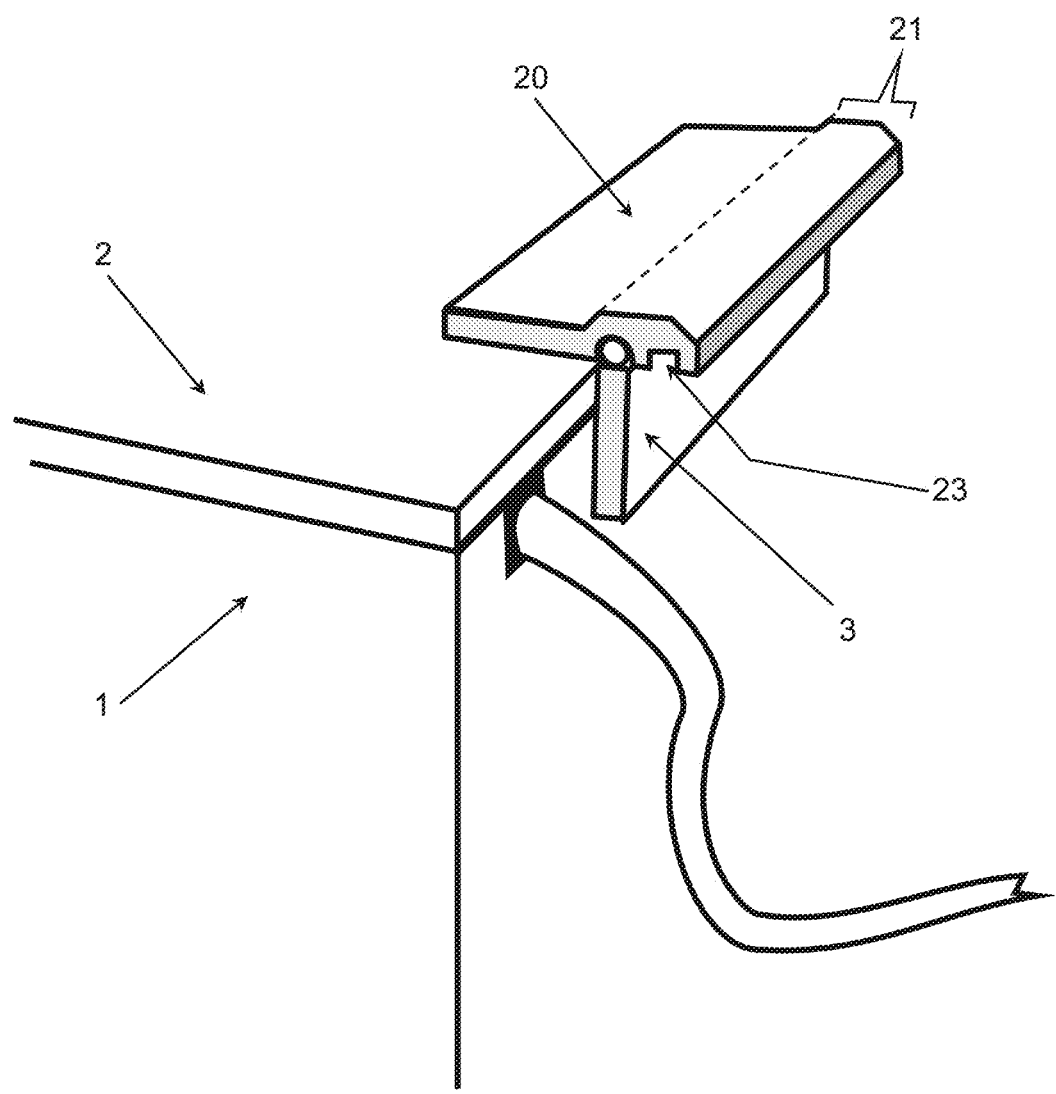
FIG. 5 is a conventional, angled, sectioned and perspective view of the box to appreciate the hinged and latch that presents the lid.

Base on the previous figures, the device for sanitizing garments and personal items comprises a box 1, preferably prismatic the upper face of which fold into the form of a lid 2, thanks to the fact that it has at least one pair of hinges 3, that allow you to open and close the box 1, in such a way that the objects to be sanitized (such as clothes, wallets, key rings, coins, containers, pantry, among others), can be introduced inside; cover 2 is closed and secured using some means of fastening A (for example, locks, snaps, hooks, zippers, adhesive or detachable tapes) in such a way that they form an airtight seal that prevents the light from coming out from inside the box 1, for this, on the periphery of the lid 2, it has an edge 4 of flexible material which is pressed with the upper edges of the box 1; inside the box 1, preferably on the rear wall, being fixed immediately under the lid 2, a first grid 5 is secured that protects a UV light emitting source 6, which emits UV light rays preferably in a range between 150 a 280 nm since, as explained, approximately 26,400 microwatt-seconds/cm2 are needed to deactivate 100% of the most resistant bacteria, but indistinctly, the light it emits can be decomposed by source 6, preferably for any of the three categories of UV light, that is, UV-A (315-400 nm), UV-B (280-315 nm) and UV-C (200-280 nm); in this way the grid 5 at each of its ends has the polarized plugs 7 and 8, to place the source 6 and energize it; a cable 9 is connected to an electronic card 10 type PCB in which are connected at least a pair of buttons 11 and 12, which can be seen from outside the box 1, in such a way that the first button 11, it turns on source 6 and the second button 12 sets the time that source 6 will be on; the card 10 also controls a pair of sensors 13 and 14, the first placed on the walls of box 1 and the second on cover 2, in such a way that when box 1 is closed, a magnetized circuit is activated and the circuit horizontal stay devices that activate a light signal 15, which can be conventional peepholes 24 to indicate that the invention is in operation, allowing the user to wait until the moment when the signal is turned off by the circuit controlled by the card 10; In case that the user inadvertently opens box 1, then the interruption of the magnetized circuit by separating the sensors 13 and 14, and lifting the cover 1 will also interrupt the horizontal stay circuit, then they will interrupt the energy with which the source 10 is turned on to prevent that the user from being exposed to UV light, by activating the time of the second bottom 12, an electronic display 16, shows a timer indicating the time remaining to finish the process; at the end of the time, the card 10 activates a conventional audible signal to indicated to the user that the lid 2 can be folded down conventionally and deactivated the magnetized circuit, turn off the source 6 and thus avoid risks for the user; therefore, in the lower part of the interior of the box 1, at the base there is a second grid 17 to hold the objects to sanitize, together with the grid 5, which cover the source 6, in this way the space inside the box 1 is optimized, to sanitize a greater amount of garments by placing them in a vertical position and holding them between the grids 5 and 17; thus, on the grid 17 a reflective cover 18 is mounted on all the interior faces of the prism that allows to generate the inclinations 19, in such a way that it directs the R rays of the source 6, towards all the sides of the interior of the box 1, which optimizes its radiation towards the garment that is contained in it and, therefore, sterilizes optimally the garment, the hinges 3, are each covered by a plate 20, which covers it, but forms a projection 21 in the same piece, which acts as a conventional stop when cover 2 is folded, preventing the lid 2, continue to rotate at the time of folding, this plate 20 can take different forms but also fulfills the function of preventing the cables and connections inside the box 1, suffer unnecessary breaks or stretching; the same plate 20, at the bottom, has a notch 23, which allows it to be locked with a conventional bolt that fits in it when the cover is opened and prevents it from falling by closing it; when the interior light is on, it can be viewed from the outside of box 1. Either by conventionally covered perforations to prevent the exit of rays and only warn that the interior light is on (the conventional perforations can be placed in the mark that the box has, just to cite an example; the same way the grille protecting the source can extend to the walls of the box allowing to notice the presence of light inside the box and the extensions can also be attached to conventional perforations in the walls and by covering them, the grille can be made of transparent material, acting as an eyewitness to the presence of light inside the box).

Having sufficiently described my invention, which I consider as a novelty and therefore a claim as my exclusive property the content of in the following claims:

1. A device to sanitize garments and personal objects, the device comprising:
   a box having an upper edge, a base, a periphery, a rear wall, a front wall, and an inside;
   a lid connected to the upper edge of the box by using hinges;
   a fastener connected to the lid, the fastener secures the lid to the box;
   a flexible material strip placed around an internal periphery of the lid to create an airtight seal when pressed to the upper edge of the box;
   a first grid located on the rear wall inside the box;
   a UV source located inside the first grid, the UV source emits UV light rays in a wavelength range between 150 and 280 nm;
   a cable connected to an electronic card, the electronic card is connected to the front wall of the box and includes at least a pair of electronic buttons;
   a first sensor located on the upper edge of the box;
   a second sensor located on the internal periphery of the lid and facing the first sensor;
   a timer connected to the electronic card and placed on the front wall of the box;
   a second grid located inside and on the base of the box, the second grid is designed to vertically hold the garments and personal objects to be sanitized, the second grid including a plurality of interior faces;
   a reflective cover placed on each one of the plurality of interior faces of the second grid, the reflective covers including inclinations that directs the UV light rays of the UV source, towards all sides of the inside of the box, which optimizes its radiation towards the garments and personal objects contained inside the box;
   wherein when the box is closed and the first sensor and the second sensor are facing each other, the electronic card activates a magnetized circuit and also a horizontal stay circuit, the horizontal stay circuit produces a luminous signal indicating that the device is in an operation mode;
   wherein when the first sensor and the second sensor stop facing each other, the device changes to a non-operation mode;
   wherein the timer indicates a reminding time for the operation mode; and
   wherein when the operation mode is completed, the electronic card activates a conventional audible signal to indicate to a user that the lid is open.

2. The device according to claim 1, further including a plate covering the hinges, wherein the plate forms a projection on the hinges that acts as a stopper when the lid is folded down preventing the lid from continuing to rotate.

3. The device according to claim 2, wherein the plate has a notch to lock the plate in place.

4. The device according to claim 1, wherein the first grid is made of a transparent material.

* * * * *